United States Patent [19]

Manker

[11] Patent Number: 5,339,796
[45] Date of Patent: Aug. 23, 1994

[54] REUSABLE WARMERS OF THE TYPE EMPLOYING A SUPER-COOLED SOLUTION AND AN ACTIVATOR

[75] Inventor: Charles F. Manker, Lake Forest, Ill.

[73] Assignee: Prism Technologies, Inc., Chicago, Ill.

[21] Appl. No.: 956,762

[22] PCT Filed: Jun. 14, 1991

[86] PCT No.: PCT/US91/04259

§ 371 Date: Dec. 7, 1992

§ 102(e) Date: Dec. 7, 1992

Related U.S. Application Data

[63] Continuation-in-part of Ser. No. 538,838, Jun. 15, 1990, Pat. No. 5,058,563.

[51] Int. Cl.$^5$ .................................................. F24J 1/00
[52] U.S. Cl. .................... 126/263 B; 126/263 DB; 126/263 DC; 252/70; 604/291
[58] Field of Search ........ 126/263 R, 263 B, 263 DB, 126/204, 263 DC; 252/70; 604/291; 128/403

[56] References Cited

U.S. PATENT DOCUMENTS

| | | |
|---|---|---|
| 3,804,077 | 4/1974 | Williams . |
| 4,077,390 | 3/1978 | Stanley et al. . |
| 4,209,413 | 6/1980 | Kent et al. . |
| 4,295,517 | 10/1981 | Guex et al. . |
| 4,338,359 | 7/1982 | Kestner . |
| 4,462,224 | 7/1984 | Dunshee et al. . |
| 4,572,158 | 2/1986 | Fiedler . |
| 4,574,051 | 3/1986 | Matthews et al. . |
| 4,596,250 | 6/1986 | Belsang, III et al. . |
| 4,756,311 | 7/1988 | Francis, Jr. . |
| 4,780,117 | 10/1988 | Lahey et al. . |
| 4,865,012 | 9/1989 | Kelley . |
| 4,872,442 | 10/1989 | Manker . |
| 4,880,953 | 11/1989 | Manker . |
| 5,058,563 | 10/1991 | Manker . |

FOREIGN PATENT DOCUMENTS

| | | |
|---|---|---|
| 57177086 | 1/1983 | Japan . |
| 57210297 | 3/1983 | Japan . |
| 63230784 | 9/1988 | Japan . |
| WO85/05440 | 12/1985 | PCT Int'l Appl. . |
| 2001057 | 7/1979 | United Kingdom . |
| 2134532 | 8/1984 | United Kingdom . |

*Primary Examiner*—Larry Jones
*Attorney, Agent, or Firm*—Leydig, Voit & Mayer, Ltd.

[57] ABSTRACT

The present invention provides reusable warmers of the supersaturated solution type that are substantially free of saddlebagging. The warmers also exhibit a more sustained period of time during which the heat pack remains within a therapeutically useful temperature range. The reusable warmers of the present invention also maintain a substantial degree of flexibility during their useful heat cycle. The reusable warmers comprise a flexible container, and located within said container, a supercooled salt solution, an activator for initiating crystallization of said supercooled salt solution, and a gelling agent, said gelling agent being present in sufficient quantity to convert said salt solution to a gel.

13 Claims, No Drawings

REUSABLE WARMERS OF THE TYPE EMPLOYING A SUPER-COOLED SOLUTION AND AN ACTIVATOR

CROSS-REFERENCE TO RELATED APPLICATIONS

This application is a continuation-in-part of U.S. application Ser. No. 538,838, filed Jun. 15, 1990 now U.S. Pat. No. 5,058,563.

FIELD OF THE INVENTION

This invention relates to reusable warmers for directly applying heat to areas of the human body to relieve muscle aches, pains and the like which employ a super-cooled aqueous solution (as for example, a super-cooled, super-saturated aqueous sodium acetate solution) and an activator to initiate the crystallization of the super-cooled liquid.

BACKGROUND OF THE INVENTION

Reusable warmers employing a super-cooled aqueous solution and an activator have been used by sportsmen and others for years to warm parts of the human body. Such a reusable warmer is shown, for example, in U.S. Pat. No. 4,077,390 to Stanley et al. (issued Mar. 7, 1978) generally at FIG. 1 and described generally at column 1, line 59 to column 2 line 4 as being a sealed bag-like flexible receptacle (such as polyethylene, nylon and the like) containing a super-cooled aqueous sodium acetate and an activator comprising a flexible metal strip having one or more slits or fissures, said patent being incorporated herein by reference. A reusable warmer having another type of activator is described in U.S. Pat. No. 4,872,442 to Manker (issued Oct. 10, 1989), said patent being incorporated herein by reference.

In reusable warmers of the present type, a super-cooled solution, such as an aqueous sodium acetate solution, is contained in a flexible receptacle, such as a bag-like receptacle. The solution is activated by flexing or bending the activator strip. Upon activation, the sodium acetate in the super-cooled solution crystallizes and heat (i.e. the "heat of crystallization") is evolved. All references herein to reusable warmer or heat packs are meant to refer to the aforementioned type of heat pack in which a supercooled solution is provided in a flexible container, which also houses a trigger or activator for initiating crystallization.

One of the primary uses for such reusable warmers is the application of heat directly to various parts of the human body for therapeutic purposes such as to relieve muscle aches and pains, to reduce inflammation and to promote healing of damaged tissue. Other uses include those by sports participants (such as hunters, skiers and the like) or sports enthusiasts (such as spectators at sporting events) who use the warmers to keep various parts of their bodies warm during cold weather.

Unfortunately, because the supercooled solution used in the warmer is water-like in consistency, it is easily drawn by gravity. The resultant flowing of the solution presents a practical problem in applying the warmer to the human body. A person using a reusable warmer may be standing, sitting or walking, while trying to apply the warmer. The gravitational pull on the fluid, however, causes the solution to flow to the lowest possible point, making application difficult, if not impossible under such conditions.

Further, because the human body, in general, is contoured and not flat, attempts to apply the present-day warmers to areas such as the knee, even when the patient is in a horizontal position, present great difficulty. Because some portion of the region to be treated always will remain in a nonhorizontal position (i.e. not flat), the liquid naturally flows away therefrom.

In particular, it has been found that during use the super-cooled aqueous solution in the present-day, reusable warmers the supercooled liquid in the plastic bag will flow, for example, around a leg or arm or knee, from areas in the bag having too much solution, leaving other areas with too little. This phenomenon has been referred to as "saddlebagging."

Saddlebagging leads to uneven coverage by the reusable warmer of the body part area to be heated. Heretofore, the art has attempted to minimize saddlebagging by various means. These have included, for example, adding welds to the flexible, sealed container of the warmer so that the solution is restrained from freely flowing. Also, the use of very heavy gauge plastics which will not only be more resistant to bending, but will also act to restrain flow of the super-cooled solution and keep a more flat surface have been tried.

None of the aforementioned solutions to the saddlebagging problem has proven satisfactory, since they render the reusable warmer less comfortable and more difficult to use. Users of the reusable warmers prefer relatively flexible containers made of relatively thin materials such as polyethylene and nylon (i.e., low cost, non vinyl packages). The more flexible the warmer, the better the contact between the warmer and the body part to be treated; however, when such thin materials are used, the super-cooled solution migrates even more, further accentuating the problem of saddlebagging.

The saddlebagging problem cannot be readily solved by conventional means, as, for example, by weld placement. Adding welds also results in a less flexible and more expensive product.

A need therefore exists for a reusable warmer of the supercooled-solution type, which eliminates or minimizes saddlebagging.

The prior art warmers also suffer from another substantial problem. Although present-day, reusable warmers tend to saddlebag while unactivated, once the super-cooled solution is activated and crystallization proceeds, the converse problem is presented. During the period from activation, through crystallization, to final cooling, present-day, reusable-warmers go through a transition from water-like consistency to that of a hard, solid lump. As the phase transition proceeds, the reusable warmer becomes more and more inflexible and difficult to shape or maintain in other than a flat configuration.

The phenomenon of hardening during the heat cycle makes it extremely difficult to maintain present-day heat packs in contact with, for example, a part of the human body such as an ankle, which is not flat. Of course, if the heat pack does not stay in contact with the region to be treated, it is of no use.

From the foregoing it is clear that a need exists for a reusable warmer of the supercooled solution-type, that maintains a substantial degree of flexibility during its useful heat cycle.

Yet another problem associated with the present-day, reusable warmers of the supercooled solution-type is that their heat is generated over a fairly short period of time after activation. Accordingly, an abrupt increase to a peak temperature is reached within only a very few minutes after activation. The warmer then immediately thereafter begins an abrupt decline in temperature. For the user, this translates into a high initial temperature followed by a cooling in a short period of time to a temperature less than desired for treating the afflicted area.

The problem, then, with the prior art warmers is that they reach a peak temperature abruptly and then immediately begin to cool quickly. A need therefore exists for a reusable warmer of the supercooled solution type having a more sustained period of time during which the heat pack remains within a therapeutically useful temperature range.

SUMMARY OF THE INVENTION

The present invention provides reusable warmers of the supersaturated solution type that are substantially free of saddlebagging. Further, the present invention provides warmers that exhibit a more sustained period of time during which the heat pack remains within a therapeutically useful temperature range. The reusable warmers of the present invention also maintain a substantial degree of flexibility during their useful heat cycle.

It has now been found that all of the aforementioned problems associated with the prior art warmers may be overcome or minimized by incorporating a sufficient amount of a gelling agent to gel the salt solution. For example, a small amount of a viscosity increasing agent may be employed, such as, for example, CELLOSIZE HEC-QP 52000-H gelling agent (Union Carbide Corporation).

The present invention thus provides a reusable warmer comprising a flexible container, and located within said container, a supercooled salt solution, an activator for initiating crystallization of said supercooled salt solution, and a gelling agent, said gelling agent being present in sufficient quantity to convert said salt solution to a gel.

The viscosity increasing, or gelling agent, agent makes the super-cooled sodium acetate solution viscous enough to delay, prevent or inhibit the natural tendency of the solution to flow around body parts which are not flat, yet allows the reusable warmer to be flexible enough so that it readily conforms to the contours of the body part to which it is being applied, making the reusable warmer more comfortable and easier to use.

Of great surprise is the fact that the use of the gelling agent also causes the product, after activation, to convert to a solid that is more flexible than that of the prior art. Advantageously, then, the heat packs of the present invention are capable of being maintained in closer contact with irregularly shaped body parts during their heat cycle, than are those heat packs of the prior art.

Also of surprise is the fact that the incorporation of the gelling agent causes a shift in the heat cycle to occur, lengthening the duration of the useful period that heat emanates from the heat pack, when compared with otherwise identical heat packs.

DESCRIPTION OF THE PREFERRED EMBODIMENT

The present invention provides improved reusable warmers, such as those containing super-cooled sodium acetate solution, and an activator (sometimes called a "trigger"). The improved warmers include a sufficient amount of a gelling agent to cause gelling of the sodium acetate or other salt solution, as by incorporating a small amount of the gelling agent (sometimes referred to as "viscosity increasing" or "thickening agents") in the super-cooled sodium acetate solution during the manufacture of the reusable warmer, which amount is sufficient to substantially inhibit the flow of the salt solution, particularly after it has been activated and is in the warm state. The exact type of viscosity increasing, gelling or thickening agent is not critical to the present invention and any number of commercially available viscosity increasing agents may be employed without departing from the spirit and scope of the invention.

The gelling agents utilized in the subject compositions can be any agent which creates a stable gel matrix, or otherwise essentially prevents flow, in the presence of substantial quantities of dissolved salt, such as sodium acetate. For example, the resultant product may be technically regarded as a pseudoplastic, but for purposes of the present invention will be considered to be a gel. Thus, to be useful in the present invention it is not necessary for a conventional gel to be formed. The useful gelling agents also include what may be technically categorized as viscosifiers and rheological control agents.

Thus, as used herein the term "gelling agent" includes conventional gelling agents, those materials which, upon contact with water, imbibe the water and thereby form hydrogels or pseudoplastics, as well as superabsorbants, which essentially prevent flow. Gelling agents of use in the present invention include both natural and synthetic materials.

Cellulose derivatives are particularly useful as gelling agents in the present invention, such as cellulose ethers, including methylcellulose, hydroxypropyl cellulose, methylhydroxypropyl cellulose, polypropyl cellulose, carboxymethyl cellulose, hydroxyethyl cellulose, hydroxymethyl cellulose, carboxymethylhydroxyethyl cellulose, hydroxypropylmethyl cellulose, hydroxyethyl propylcellulose, and hydroxybutyl methylcellulose. Examples of superabsorbants useful as gelling agents in the practice of the present invention, which actually absorb liquid and can absorb up to 1000 times their weight of water, are starch graft copolymers, such as hydrolyzed acrylonitrile grafted starch, and polyacrylate grafted starch,. U.S. Pat. Nos. 4,435,488; 4,455,358, and 4,563,404, all of which are incorporated herein by reference, disclose gelling agents of the type contemplated for such use herein and the these patents are incorporated herein by reference.

Natural and synthetic gums and gum-like materials may also be employed as gelling agents in the present invention, such as Irish moss, gum tragacanth, Viscarin GMC, Kappa- and Iota carrageenan, sodium alginate, guar, hydroxypropyl guar, carboxymethyl-hydroxypropyl guar, hydroxy ethyl guar, alginates, carrageenan, xanthan gum, gelatin, agarose, gum arabic, carob, tragacanth, locust bean gum, karaya, pectin, agar, gum acacia, tara gum, polysuccrose, polyglucose, and Zooglan (the exocellular polysaccharide isolated from *Zoogloea ramigera*.

The gelling agents also may be any synthetic polymer or copolymer which is hydratable and cross-linkable in solution, such as polymers which contain one or more of the following functional groups: hydroxyl, cis-hydroxyl, carboxyl, sulfate, sulfonate, amino or amide. Examples of these synthetic polymers include, but are not limited to, polyacrylates, polymethylacrylates, polyacrylamides, acrylamide methyl propane sulfonic acid copolymers, polyvinyl alcohols, maleic anhydride-based copolymers such as poly(methylvinylether-maleic anhydride), ethylene maleic anyhdride, and maleic anhydride methylvinyl ether copolymers, polyvinyl pyrollidone, polyvinyl alcohol, polyacrylic acid, copolymers of acrylic acid and a polyallyl sucrose such as Carbomer 934, also known as Carbopol 934 and available from B. F. Goodrich Chemical Company, polyoxyethylene-polyoxypropylene diol block copolymers which are commercially available as the Pluronics from BASF-Wyandotte. carboxypolymethylene, and polyacrylamide.

Other suitable gelling agents may be selected by reference to published literature, such as the *Kirk-Othmer Encyclopedia of Chemical Technology*, Vol. 20, 207–230, dealing with water soluble resins, which text is incorporated herein by reference.

One preferred class of gelling agents are the poly-(ethylene oxide) polymers, such as those supplied under the trademark POLYOX by Union Carbide Corporation.

Another example of a particularly well-suited type of gelling agent is that sold by Union Carbide Corporation under the trademark CELLOSIZE. They are hydroxyethyl cellulose (HEC) gelling agents which are nonionic, water-soluble polymers. As indicated above, other water-soluble natural polymers (such as the gums, starches, celluloses, gelatin, etc.) and other chemically modified derivatives of the same which are commonly used as thickeners, suspending agents, gelling agents, emulsifiers or dispersants may also be employed, provided that the material causes the solution to gel or increase in viscosity sufficiently to inhibit or slow-down the flow of the solution during the heat producing phase.

The method of making a reusable warmer is well known and does not form an essential part of the herein-described invention. Any of several methods of manufacture can be employed as, for example, that which is described in the aforementioned U.S. Pat. No. 4,077,390 at columns 2 and 3. Further, the type of activator used also is not an essential part of the present invention and any suitable activator or trigger can be used, as, for example, the activators described in the aforementioned U.S. Pat. No. 4,077,390 or 4,872,442.

The essential element is the incorporation of a sufficient amount of a gelling agent to cause the supercooled sodium acetate solution to form a gel, such as a small amount of a viscosity increasing agent (such as, for example, Union Carbide's CELLOSIZE gelling agent), during manufacture of the reusable warmer. The amount of viscosity increasing, thickening or gelling agent used can vary depending upon the specific type of reusable warmer being made. However, the amount used should not be so small that the viscosity of the super-cooled sodium acetate solution is so low that the solution flows to an appreciable extent and collects in low spots in the bag (and cause saddle bagging), nor should it be so great that the viscosity of the super-cooled solution is so high that the reusable warmer is not flexible and, therefore, not comfortable to use. Thus, when reference is made herein to a gel, the term is to be understood as meaning a soft gel which remains deformable.

It has been found that when hydroxyethyl cellulose is used as the viscosity increasing agent, the amount of gelling agent used can be less than about 5% by weight of the supercooled solution and, preferably, between about 1 to 4% by weight. Of course, as is true with all polymeric materials, there is a relationship between the molecular weight of the polymer and its viscosity or ability to form a gel in solution.

With respect to CELLOSIZE HEC, it is preferable to use those grades with the higher molecular weights, such as grades QP 52000 or 100 MH, which have the highest molecular weight. When such grades are used, the amount employed will be less than if the lower molecular weight grades are used. Reference to the published manufacturer's literature regarding the relationship between the different grades and their viscosity as 1% aqueous solutions may be made to assist in determining optimum levels of use.

The salt used to form the supercooled solution may be any of the art-recognized salts which are capable of forming a supercooled solution. The preferable salt is sodium acetate because it is relatively inexpensive and innocuous. The amount of sodium acetate is not critical. In general, the amount of sodium acetate will range from about 40 to about 50 percent.

The construction of the container also is not critical. Typically the container will be in the shape of a bag and will be constructed of any suitable material. Transparent films, which may be multilaminates, are preferred. The films preferably have at least one side that may be heat-sealed. It is preferred to use nylon-polyethylene laminate as the flexible film.

The invention can further be best described by the following examples.

EXAMPLE 1

Into an empty vinyl bag sealed along three sides, there was introduced a 50% sodium acetate solution at 200 degrees Fahrenheit containing 3 percent, by weight, CELLOSIZE HEC-52000-H (Union Carbide Corporation), in an amount sufficient to fill the bag, and an activator of the type generally described in U.S. Pat. No. 4,872,442. The bag was then totally sealed and allowed to cool at ambient temperature over a period of about two (2) hours. The cooling time could be reduced by immersion of the warmer in cold water or by placing it in a refrigerator. After the two hours a viscous super-cooled sodium acetate solution formed which was gelatinous in nature. The gelatinous super-cooled solution was generally clear and transparent and the activator inside the reusable warmer readily could be seen.

When the reusable warmer was activated (by flexing the activator) it provided the same level of warmth for the same period of time as did similar reusable warmers which did not contain any CELLOSIZE HEC-QP 52000-H. The thickened or gelatinous supercooled sodium acetate solution was stable (it did not separate into its component parts) and did not attack the container. The concentration of the super-cooled salt solution can be varied depending on the temperature to be achieved by activation. It was found that the gelatinous super-cooled solution cushioned and suspended the activator so that the danger of accidental activation during manufacture, shipping or storing of the reusable warmer was substantially reduced.

EXAMPLE 2

A reusable warmer was assembled similar to the one in Example 1, except 2 to 3% by weight of CELLOSIZE HEC-QP 100000-H (Union Carbide Corporation) was employed instead of the CELLOSIZE HEC-QP 52000-H used in Example 1. As in Example 1, a viscous super-cooled sodium acetate solution formed which was gelatinous in nature. The gelatinous super-cooled solution was generally clear and transparent and the activator inside the reusable warmer readily could be seen.

When the reusable warmer was activated (by flexing the activator) it provided the same level of warmth for the same period of time as did similar the reusable warmer of Example 1. The thickened or gelatinous super-cooled sodium acetate solution was stable (it did not separate into its component parts) and did not attack the container.

EXAMPLE 3

A reusable warmer was assembled similar to the one in Example 1, except that between 10–30% by weight of a corn starch was used as the viscosity increasing agent. During assembly of the reusable warmer, considerable care must be taken in mixing in the starch because it tended to form lumps easily. Mixing was performed using high shear mixers. The assembled reusable warmer, after heating, was not as clear as the reusable warmers of Examples 1 and 2. However, its stability was good.

The reusable warmer of the present invention can be used as a "cold pack" by placing it in a refrigerator for a short period. It is apparent that the salt (sodium acetate) contained in the cold pack sufficiently reduces the freezing temperature of the water so that freezing does not take place. When used in this fashion the cold pack has many of the same advantages that it has when used as a reusable warmer; it holds temperature well and conforms to the area of the body to which it is applied. The stability of the cold pack when used in this fashion is highly dependent on the purity of the water and the acetate used in its manufacture; the greater the purity of the solution, the lower the temperature at which the cold pack can be used. For temperatures down to 25 degrees Fahrenheit tap water and standard, acetate is acceptable.

EXAMPLE 4

To compare the temperature-time relationship during the heating cycle between a reusable warmer of the present invention having a gelling agent and one of the prior not employing a gelling agent, the following experiment was conducted.

One set of three inch by four inch bags were filled with two ounces of gel solution made in accordance with Example 2 and another set were filled with two ounces of solution identical to the first set, but not containing a gelling agent. Both sets of bags had initial starting temperatures of 81° F. and were activated, attaining peak temperatures of 107° F. An infrared thermometer was then used to measure surface temperatures every two minutes, for a period of twenty minutes. During this time the bags containing the gelling agent were two-three degrees warmer at all times than the bags that did not contain a gelling agent. The foregoing demonstrates that the reusable warmers of the present invention demonstrate a more desirable heat profile during crystallization, than the reusable warmers of the prior art.

EXAMPLE 5

To compare the flexibility, during the heating cycle, and at the end thereof, between a reusable warmer of the present invention having a gelling agent and one of the prior not employing a gelling agent, the following experiment was conducted.

The same sets of bags as employed in Example 4 were tested for their ability to conform to and hold a shape during the heating cycle, by placing the bags around a 0.75 inch diameter dowl rod. The bags containing the gelling agent held their shape considerably better than the bags that did not contain the gelling agent. It was also found that the bags containing the gelling agent remained relatively stationary throughout the wrapping and draping process, whereas the bags that did not contain the gelling agent did not. The bags containing the gelling agent also had a cushion-like feel and response whereas the bags that did not contain the gelling agent had no "body" to them at all.

The wrapping and draping around the dowl rod simulates procedures that would be performed in a hospital setting. Thus, the foregoing demonstrates that the reusable warmers of the present invention demonstrate better flexibility during and after crystallization, when compared to the reusable warmers of the prior art.

It will be apparent to those skilled in this art that various changes may be made in the construction and form of the reusable warmer employing a gelatinous super-cooled solution and in the details of the method of manufacture without departing from the spirit and scope of this invention, and that the specific directions and forms shown herein are presented for the purpose of making an understandable disclosure of the invention and are not intended to be any restriction on the scope thereof, other than as defined in the accompanying claims.

EXAMPLE 6

To demonstrate the utility of the natural and synthetic gums as gelling agents used in the present invention, the following experiment using xanthan gum was conducted.

To several three inch by four inch bags containing a premixed sodium acetate solution, five percent, by weight, xanthan gum (supplied by Kelco) was added. After addition of the xanthan gum, the solution gelled very well, however, the color was extremely dark, forming an almost brown, opaque composition. The bags were subsequently activated and performed similarly to the bags of Example 4 containing the gelling agent.

What is claimed is:

1. A reusable warmer comprising a flexible container, and located within said container, a supercooled salt solution of sodium acetate, an activator for initiating crystallization of said supercooled salt solution of sodium acetate, and a gelling agent, said gelling agent being present in sufficient quantity to convert said salt solution to a gel which remains deformable after crystallization of said salt solution.

2. The reusable warmer of claim 1 wherein the gelling agent is a non-ionic, water-soluble hydroxyethylcellulose polymer.

3. The reusable warmer of claim 1 wherein the gelling agent is selected from the group consisting of cellulose ethers.

4. The reusable warmer of claim 3 wherein the gelling agent is selected from the group consisting of methylcellulose, hydroxypropyl cellulose, methylhydroxypropyl cellulose, polypropyl cellulose, carboxymethyl cellulose, hydroxyethyl cellulose, and hydroxymethyl cellulose, carboxymethylhydroxyethyl cellulose, hydroxypropylmethyl cellulose, hydroxyethyl propylcellulose, and hydroxybutyl methylcellulose.

5. The reusable warmer of claim 1 wherein the gelling agent is selected from the group consisting of starch graft copolymers.

6. The reusable warmer of claim 1 wherein the gelling agent is selected from the group consisting of natural and synthetic gums.

7. The reusable warmer of claim 6 wherein the gelling agent is selected from the group consisting of Irish moss, gum tragacanth, viscarin GMC, kappa- and iota carrageenan, sodium alginate, guar, hydroxypropyl guar, carboxymethyl-hydroxypropyl guar, hydroxy ethyl guar, alginates, carrageenan, xanthan gum, gelatin, agarose, gum arabic, carob, tragacanth, locust bean gum, karaya, pectin, agar, gum acacia, tara gum, polysuccrose, polyglucose, and zooglan.

8. The reusable warmer of claim 1 wherein the gelling agent is selected from the group consisting of synthetic polymers and copolymers which are hydratable and cross-linkable in solution.

9. The reusable warmer of claim 8 wherein the gelling agent is selected from the group consisting of polyacrylates, polymethylacrylates, polyacrylamides, acrylamide methyl propane sulfonic acid copolymers, polyvinyl alcohols, maleic anhydride-based copolymers, polyvinyl pyrollidone, polyvinyl alcohol, polyacrylic acid, copolymers of acrylic acid and a polyallyl sucrose, polyoxyethylene-polyoxypropylene diol block copolymers carboxypolymethylene, and polyacrylamide.

10. The reusable warmer of claim 1 wherein the gelling agent is selected from the group consisting of poly(ethylene oxide) polymers.

11. The reusable warmer of claim 1, wherein said sodium acetate is present in an amount of from about 40% to about 50% by weight.

12. The reusable warmer of claim 1, wherein said sodium acetate is present in an amount of about 40% by weight.

13. The reusable warmer of claim 1, wherein said sodium acetate is present in an amount of about 50% by weight.

* * * * *